United States Patent [19]
Ellingsen et al.

[11] Patent Number: 5,571,188
[45] Date of Patent: Nov. 5, 1996

[54] PROCESS FOR TREATING A METALLIC SURGICAL IMPLANT

[75] Inventors: Jan E. Ellingsen, Bekkestua; Gunnar Rolla, Oslo, both of Norway

[73] Assignee: Astra Aktiebolag, Sodertalje, Sweden

[21] Appl. No.: 446,790

[22] PCT Filed: Dec. 1, 1993

[86] PCT No.: PCT/SE93/01032

§ 371 Date: May 30, 1995

§ 102(e) Date: May 30, 1995

[87] PCT Pub. No.: WO94/13334

PCT Pub. Date: Jun. 23, 1994

[30] Foreign Application Priority Data

Dec. 4, 1992 [NO] Norway ................................. 924697

[51] Int. Cl.⁶ .......................... A61L 27/00; B05D 3/10
[52] U.S. Cl. .......................... 623/16; 427/2.26; 427/435
[58] Field of Search .......................... 427/2.26, 2.27, 427/435, 2.24; 106/35; 623/16

[56] References Cited

U.S. PATENT DOCUMENTS

| | | | |
|---|---|---|---|
| 3,978,206 | 8/1976 | Naumann et al. | 424/49 |
| 4,097,935 | 7/1978 | Jarcho | 106/35 |
| 4,846,897 | 7/1989 | Nakagawa et al. | 148/251 |
| 4,880,660 | 11/1989 | Aasen et al. | 427/2.26 |
| 5,032,129 | 7/1991 | Kurze et al. | 623/16 |
| 5,039,546 | 8/1991 | Chung et al. | 427/2 |
| 5,106,304 | 4/1992 | Chronister | 106/35 |
| 5,209,829 | 5/1993 | Gondel et al. | 204/129.75 |
| 5,211,833 | 5/1993 | Shirkhanzadeh | 205/322 |
| 5,322,110 | 6/1994 | Wall et al. | 164/100 |

OTHER PUBLICATIONS

"Experimental Study on Hydroxyapatite Soaked in Sodium Fluoride", Abstract No. 241877k, Nippon Seikeigeka Gakkai Zasshi 65(12), 1199–210, International, File CA, Chemical Abstracts, vol. 116, No. 24, 15 Jun. 1992.

*Primary Examiner*—Diana Dudash
*Attorney, Agent, or Firm*—Fish & Richardson P.C.

[57] ABSTRACT

Metallic surgical implant materials having improved strength of connection with bone are produced when the implants are treated prior to implantation with an aqueous solution of sodium fluoride.

22 Claims, No Drawings

PROCESS FOR TREATING A METALLIC SURGICAL IMPLANT

This invention relates to a process for treating a metallic surgical implant, particularly an implant made of titanium or a titanium alloy.

BACKGROUND OF THE INVENTION

Titanium and titanium alloys are frequently used as implant materials in dental and orthopedic surgery because of their good compatibility with bone tissue and thir tendency to form a firm attachment directly with bone tissue. The interaction between bone tissue and metal, leading to such firm attachment, was coined "osseointegration" by Brinemark and co-workers, of Gothenburg, Sweden, in the late 1970's, but the mechanics of the attachment process are not yet fully understood.

The standard surgical technique for fixing a surgical implant involves a two-stage process. In the first stage the soft tissue covering the bone tissue is opened and a base pan of the implant is placed in the bone tissue. The soft tissue is closed and the implant left to osseointegrate for a comparatively long period of time. In the second stage the soft tissue is re-opened and the load-bearing parts of the implant are attached to the base part A two-stage technique such as this has some disadvantages, since the long period needed for osseointegration is very uncomfortable for the patient Furthermore, in orthopaedics it is preferable to have a one-stage operation since a joint, for example the hip joint, should not be operated on twice if this can be avoided. One prerequisite of a one-stage operation is that the time needed to obtain sufficient strength at the bone tissue -implant interface, is short. In addition, there may be problems in obtaining a full osseointegration in those cases where the quality of the bone is poor or the available space is limited, for example in the upper jaw or in the posterior parts of the lower jaw above the nerve. In these places it would therefore be desirable to stimulate the regeneration of the bone tissue around the implant.

There are to date several methods for treating implants made of titanium in order to obtain a better attachment of the implant. Some of these involve altering the topography of the implant, for example by creating relatively large irregularities on the implant surface in order to obtain a better mechanical retention and to increase the area of attachment, by for example plasma spraying, blasting or etching. Although the retention may be improved, the time necessary for the osseointegration process may be longer since the bone tissue would have to grow into the irregularities in the surface.

Other methods involve altering of the chemical properties of the implant surface. For example one such method involves the application of a layer of ceramic material such as hydroxyapatite to the implant surface, inter alia in order to stimulate the regeneration of the bone tissue. Ceramic coatings however may be brittle and may flake or break off from the implant surface, which may in turn lead to the ultimate failure of the implant.

U.S. Pat. No. 4,330,891 could perhaps be said to combine each of the above, in that the provision of an element with a micro-pitted surface which micro-pits are within a certain diameter range, is said to effect improved properties as regards acceptance of the carrier element, and primarily improved durability of the healthy ingrowth of the element due to its biological quality.

THE INVENTION

It is the object of the present invention to provide a metallic surgical implant having improved strength of connection with bone. This object is achieved by treating a metallic surgical implant with a solution of sodium fluoride according to the present invention.

According to the present invention, therefore, there is provided a process for treating a metallic surgical implant prior to implantation, comprising treating the said implant with an aqueous solution containing a soluble fluoride salt, which solution is of pH 2.5 to pH 6.

Preferably, the aqueous solution is of pH 2.5 to pH 5.

The present invention is particularly of interest in the treatment of titanium or titanium alloy, such as Ti/Al/V alloy, implants, but may also be employed for the treatment of other metallic implants such as those of zirconium and tantalum, and coated metallic implants such as hydroxyapatite-coated titanium.

The treatment solution preferably contains sodium fluoride in a concentration of 0.1% to saturated, such as 0.4% to saturated, or 0.5% to saturated. Most preferably the sodium fluoride is present in substantially saturated mount at room temperature, such as 4% at room temperature.

Treatment of the metallic surgical implant may be carried out in any suitable manner, for example by immersing the implant in the treatment solution for a period of me and with or without agitation. Varying temperatures may be employed; parameters such as temperature and time may be selected according to the concentration of the treatment solution and the other process parameters. In most cases, for treatments at room temperature, treatment should be carried out for at least ten seconds such as from ten seconds to sixty minutes; in the case of a saturated solution of fluoride, treatment at room temperature for around five minutes is preferable. Treatment is conveniently carried out at standard pressure, but elevated pressures may be used where desired. Preferably, treatment is carried out at standard pressure and temperature.

The treatment solution of the present invention may be simply prepared, by dissolving the appropriate amount of sodium fluoride in water. The pH may be lowered by small additions of acid, such as HF or HCl, and if required small amounts of base may be added to raise the pH.

Prior to treatment, the implant material may be cleaned by standard techniques such as are well known in the art.

After treatment, the implant material may be washed in distilled water and kept under sterile conditions.

In titanium implants treated according to the present invention, a force four times greater than that needed to displace untreated implants, was required in order to displace the said implants from bone. The implants tested were conical in shape such that mechanical and frictional influences were minimised. It is believed that the improved properties found in implants treated according to the present invention are the result of improved biocompatibility and osseointegration resultant from the treatment process. While we do not wish to be limited to the expression of theories herein, the improved biocompatibility is thought to be due, at least in part, to fluoride being retained on the surface of the treated implant.

The invention will now be illustrated by Example.

EXAMPLES

Comparative Example

Six surgical implants, of commercially pure (c.p.) titanium. 5 mm in length and generally conical in shape having a diameter at one end of 3 mm and at the other end 2 mm, were prepared by machining using a "Maximat super 11" (TM) turning lathe. Therefore the area of the conical sides of the implant. i.e. the pan of the implant to be located in the bone, is 39 mm².

Each implant was cleaned according to a well-known cleaning procedure involving the following steps:
1. Treatment with trichloroethylene with ultrasonic treatment, for 15 minutes.
2. Rinsing in absolute ethanol, for 10 seconds.
3. Three successive treatments with ethanol with ultrasonic treatment each for 10 minutes.

Each cleaned implant was sterile packaged in a Mediplast (TM) sterile envelope, and autoclaved in a Citomat 162 (TM) (LIC Company) autoclave, at 120° C. for 30 minutes.

EXAMPLE 1

A sodium fluoride bath was prepared simply by dissolving sodium fluoride crystals in distilled water, to give a 4% solution. The pH of the bath was adjusted to pH 3.7 with 6N hydrochloric acid.

Six implants, prepared, cleaned, sterile packaged and autoclaved exactly as in the Comparative Example above, were removed from their sterile packages, placed in the sodium fluoride treatment bath and left there for ten minutes. Thereafter each was washed three times in a bath of distilled water, for periods of 30 seconds each wash. After being allowed to dry at room temperature, each implant was transferred to a Mediplast (TM) sterile envelope to await surgical implantation.

IMPLANT STUDY

Chinchilla rabbits were used as test animals. The rabbits were randomly distributed regarding sex, but all had a weight of 2.5 kg at the start of the study. Each animal was sedated by injection using a combination of fluanozonium 1.0 mg/kg and fentanylium 0.02 mg/kg (Hypnorm, Jannsen Pharmaceuticals, Belgien) and locally anesthetised with xylocaine/adrenaline (AB Astra). Two cavities were drilled in each rabbit's right ulna, using standardised bores designed to provide cavities into which the conical implants would exactly fit. Implants according to the Comparative Example or Example 1 were placed in the cavities of each rabbit, using titanium tweezers so as to avoid the influence of other metals, and left for sixty days.

At the end of sixty days the rabbits were sacrificed by injection with pentobarbitol natrium, and the ulna's removed and placed in sterile physiological saline to await a "push-out" test the same day.

An Instron model 1121 tensile testing machine (Instron, U.K.) inter alia comprising a support jig and a ram adjusted for a load range of 0–200N, was employed to measure the maximum force needed to separate each implant from bone. Milling tracks, to fit the support jig, were made in the specimen to be tested, in the bone surrounding the larger end of the implant, and the specimen was placed on the support jig. The ram was lowered at a speed of 1 mm/min., and the maximum force required to separate the implant from the bone was recorded.

This recorded pressure gives a direct assessment of the strength of connection of the implant and bone, the higher the required force the stronger the connection.

The results are recorded in Table 1.

TABLE 1

| Recorded force (N) | | | |
|---|---|---|---|
| Implants according to the Comparative Examples | | Implants according to Example 1 | |
| 1 | 37.0 | 1 | 105.0 |
| 2 | 47.5 | 2 | 121.0 |
| 3 | 24.5 | 3 | 100.0 |
| 4 | 11.5 | 4 | 118.2 |
| 5 | 28.5 | 5 | 125.0 |
| 6 | 16.0 | 6 | 128.0 |
| mean | 27.5 | mean | 116.2 |

The much greater strength of bone connection with implants treated in accordance with the present invention is apparant from the above.

Histological examination demonstrated that the implants according to Example 1 were surrounded even in the ulna's spongiosa by a thick layer of newly formed bone which was in close contact with the implants. In contrast the untreated implants, i.e. those according to the Comparative Examples, were only partly covered, by a thin bone layer, in the spongiosal area.

We claim:

1. A process for treating a metallic surgical implant prior to implantation, which implant is not coated with a calcium phosphate coating, comprising treating a metallic surface of said implant with an aqueous solution containing sodium fluoride, which solution is of pH 2.5 to pH 6.

2. A process according to claim 1, wherein the aqueous solution is of pH 2.5 to pH 5.

3. A process according to claim 1, wherein the metallic surgical implant comprises titanium or a titanium alloy.

4. A process according to claim 1, wherein the concentration of sodium fluoride in the solution is in the range 0.1% to saturated.

5. A process according to claim 4, wherein the concentration of sodium fluoride in the solution is in the range 0.4% to saturated.

6. A process according to claim 4, wherein the sodium fluoride solution is substantially saturated at room temperature.

7. A process according to claim 4, wherein the concentration of sodium fluoride in the solution is approximately 4% at room temperature.

8. A process according to claim 1, wherein the pH of the solution is approximately 3.7.

9. A process according to claim 1, wherein said treatment comprises immersing the implant in the aqueous solution at room temperature for a period of at least ten seconds.

10. A process according to claim 1, wherein said treatment comprises immersing the implant in the aqueous solution at room temperature for ten seconds to five minutes.

11. A process according to claim 1, wherein said treatment comprises immersing the implant in the aqueous solution of sodium fluoride at room temperature for a period of approximately five minutes.

12. A metallic surgical implant treated by the process of claim 1.

13. A surgical implant according to claim 12, wherein the aqueous solution is of pH 2.5 to pH 5.

14. A surgical implant according to claim 12, wherein the metallic surgical implant comprises titanium or a titanium alloy.

15. A surgical implant according to claim 12, wherein the concentration of sodium fluoride in the solution is in the range 0.1% to saturated.

16. A surgical implant according to claim 15, wherein the concentration of sodium fluoride in the solution is in the range 0.4% to saturated.

17. A surgical implant according to claim 15, wherein the sodium fluoride solution is substantially saturated at room temperature.

18. A surgical implant according to claim 15, wherein the concentration of sodium fluoride in the solution is approximately 4% at room temperature.

19. A surgical implant according to claim 12, wherein the pH of the solution is approximately 3.7.

20. A surgical implant according to claim 12, wherein said treatment comprises immersing the implant in the aqueous solution at room temperature for a period of at least ten seconds.

21. A surgical implant according to claim 12, wherein said treatment comprises immersing the implant in the aqueous solution at room temperature for ten seconds to five minutes.

22. A surgical implant according to claim 12, wherein said treatment comprises immersing the implant in the aqueous solution of sodium fluoride at room temperature for a period of approximately five minutes.

* * * * *